(12) United States Patent
Weitzner

(10) Patent No.: US 11,992,224 B2
(45) Date of Patent: *May 28, 2024

(54) TETHER TRACTION SYSTEMS AND METHODS OF USE THEREOF

(71) Applicant: Boston Scientific Scimed, Inc., Maple Grove, MN (US)

(72) Inventor: Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/940,676

(22) Filed: Sep. 8, 2022

(65) Prior Publication Data

US 2023/0000496 A1     Jan. 5, 2023

Related U.S. Application Data

(63) Continuation of application No. 15/930,607, filed on May 13, 2020, now Pat. No. 11,464,520.

(60) Provisional application No. 62/861,555, filed on Jun. 14, 2019.

(51) Int. Cl.
    *A61B 17/128* (2006.01)
(52) U.S. Cl.
    CPC ............................ *A61B 17/1285* (2013.01)
(58) Field of Classification Search
    CPC ............ A61B 1/00101; A61B 1/00137; A61B 17/1227; A61B 17/1285; A61B 2017/00292
    See application file for complete search history.

(56) References Cited

U.S. PATENT DOCUMENTS

| | | |
|---|---|---|
| 7,060,024 B2 | 6/2006 | Long et al. |
| 7,060,025 B2 | 6/2006 | Long et al. |
| 7,758,593 B2 | 7/2010 | Nobis et al. |
| 7,815,565 B2 | 10/2010 | Stefanchik et al. |
| 8,029,504 B2 | 10/2011 | Long |
| 8,062,311 B2 | 11/2011 | Itscher et al. |
| 8,425,505 B2 | 4/2013 | Long |
| 8,449,538 B2 | 5/2013 | Long |
| 10,251,645 B2 | 4/2019 | Kostrzewski |
| 10,791,911 B2 | 10/2020 | Wales et al. |
| 10,952,717 B2 | 3/2021 | Rodriguez Salazar et al. |

(Continued)

FOREIGN PATENT DOCUMENTS

| | | |
|---|---|---|
| EP | 1852073 A1 | 11/2007 |
| EP | 2120758 A2 | 11/2009 |

(Continued)

OTHER PUBLICATIONS

International Search Report and Written Opinion for Application No. PCT/US2020/032579, dated Jul. 23, 2020, 18 pages.

*Primary Examiner* — Ryan J. Severson
(74) *Attorney, Agent, or Firm* — Seager, Tufte & Wickhem, LLP

(57) ABSTRACT

The present disclosure relates generally to the field of medical devices. In particular, the present disclosure relates to traction systems, and methods of use thereof, for endoscopic procedures such as tissue dissection. For example, a traction system may include a filament extendable along an outer surface of an endoscope with a distal end of the filament attachable to a medical device engaged with a target tissue of a body lumen.

20 Claims, 4 Drawing Sheets

(56) References Cited

U.S. PATENT DOCUMENTS

| | | |
|---|---|---|
| 11,147,564 B2 | 10/2021 | Bagley et al. |
| 11,464,520 B2 * | 10/2022 | Weitzner ............ A61B 1/00101 |
| 2004/0230096 A1 | 11/2004 | Stefanchik et al. |
| 2005/0107809 A1 | 5/2005 | Litscher et al. |
| 2007/0260264 A1 | 11/2007 | Nobis et al. |
| 2007/0270894 A1 | 11/2007 | Zimmon |
| 2008/0177135 A1 | 7/2008 | Muyari et al. |
| 2008/0200912 A1 | 8/2008 | Long |
| 2010/0087813 A1 | 4/2010 | Long |
| 2010/0130975 A1 | 5/2010 | Long |
| 2011/0124961 A1 | 5/2011 | Zimmon |
| 2011/0306971 A1 | 12/2011 | Long |
| 2012/0065647 A1 | 3/2012 | Itscher et al. |
| 2013/0261389 A1 | 10/2013 | Long |
| 2014/0228634 A1 | 8/2014 | Zimmon |
| 2015/0282813 A1 | 10/2015 | Litscher et al. |
| 2016/0296280 A1 | 10/2016 | Long |
| 2017/0258460 A1 | 9/2017 | Zimmon |
| 2017/0354408 A1 | 12/2017 | Kostrzewski |
| 2018/0000321 A1 | 1/2018 | Wales et al. |
| 2018/0263614 A1 | 9/2018 | Lee et al. |
| 2020/0022705 A1 | 1/2020 | Litscher et al. |
| 2020/0129181 A1 | 4/2020 | Carrillo, Jr. et al. |
| 2020/0360005 A1 | 11/2020 | Rodriguez Salazar et al. |
| 2020/0360006 A1 | 11/2020 | Sluti et al. |
| 2020/0360023 A1 | 11/2020 | Bagley et al. |
| 2020/0390446 A1 | 12/2020 | Weitzner |
| 2021/0338046 A1 * | 11/2021 | Yahagi ............ A61B 17/00234 |
| 2023/0000496 A1 * | 1/2023 | Weitzner ............ A61B 17/1227 |

FOREIGN PATENT DOCUMENTS

| | | |
|---|---|---|
| EP | 3257448 A2 | 12/2017 |
| JP | H10-290803 A | 11/1998 |
| JP | 2014171629 A | 9/2014 |
| WO | 2018006044 A1 | 1/2018 |

* cited by examiner

TETHER TRACTION SYSTEMS AND METHODS OF USE THEREOF

CROSS-REFERENCE TO RELATED APPLICATIONS

This application is a continuation of and claims the benefit of the earlier filing date of U.S. patent application Ser. No. 15/930,607, filed on May 13, 2020, which claims the benefit of priority under 35 U.S.C. § 119 to U.S. Provisional Patent Application No. 62/861,555, filed on Jun. 14, 2019, and which applications are incorporated herein by reference in their entireties for all purposes.

FIELD

The present disclosure relates generally to the field of medical devices. In particular, the present disclosure relates to traction systems, and methods of use thereof, for endoscopic procedures such as tissue dissection.

BACKGROUND

Performing an endoscopic tissue resection/dissection procedure may include maintaining traction as the boundaries of the target tissue are dissected for accuracy and efficiency of the procedure. Physicians may use a tethered system in which an endoscopic clip is attached to a length of filament extending external to the patient to retract/immobilize a target tissue for dissection along the tissue margins and/or to retrieve the dissected target tissue for biopsy.

It is with the above considerations in mind that the improvements of the present disclosure may be useful.

SUMMARY

In one aspect, the present disclosure relates to a system for use with an endoscope comprising a cap attachable to (or a portion of) a distal end of an endoscope having a working channel extending therethrough. The cap may include a lumen coextensive with the working channel. A first guide may be attached to/mounted on an outer surface of the cap. A first filament may be extendable through the first guide and along an outer surface of the endoscope and the cap. A first endoscopic instrument may be disposable within the working channel. A distal end of the first filament may be attached to a distal end of the first endoscopic instrument.

In the described and other embodiments, the first endoscopic instrument may include a sheath and a first medical device may be releasably attached to a distal end of the sheath. The first medical device may include a tissue clamp. The distal end of the first filament may be attached to an arm of the tissue clamp. A handle may be operatively attached to a proximal end of the first endoscopic instrument. The handle may be configured to move the first medical device between a first and second position. The handle may be configured to release the first medical device from the distal end of the sheath. A flexible elongate shaft may be extendable along the outer surface of the endoscope and the cap and through the first guide. The first filament may extend through the flexible elongate shaft. A handle assembly may be attachable to a proximal end of the flexible elongate shaft. The handle assembly may include first, second, and third gripping elements. The first gripping element may be configured to advance and retract the flexible elongate shaft through the first guide. The second and third gripping elements may be attached to each other by a connector. A proximal end of the first filament may be attached to the connector.

In another aspect, the present disclosure relates to a system for use with an endoscope comprising a cap attachable to (or a portion of) a distal end of an endoscope having a working channel extending therethrough. The cap may include a lumen coextensive with the working channel. A first guide and a second guide may be attached to/mounted on an outer surface of the cap. A first filament may be extendable through the first guide and along an outer surface of the endoscope and the cap. A first endoscopic instrument may be disposable within the working channel. A distal end of the first filament may be attached to a distal end of the first endoscopic instrument.

In the described and other embodiments, the first endoscopic instrument may include a sheath and a first medical device may be releasably attached to a distal end of the sheath. The first medical device may include a tissue clamp. The distal end of the first filament may be attached to an arm of the tissue clamp. A second filament may extend through the second guide and along an outer surface of the endoscope and the cap. A distal end of the second filament may be attached to an arm of a second medical device. A flexible elongate shaft may extend along the outer surface of the endoscope and the cap and through the first guide. The first filament may extend through the flexible elongate shaft. A flexible elongate shaft may be extendable along the outer surface of the endoscope and the cap and through the second guide. The second filament may extend through the flexible elongate shaft.

In another aspect, the present disclosure relates to a system for performing an endoscopic procedure. The system may comprise a first guide extendable along an outer surface of the endoscope. The guide may be configured for mounting on an endoscope or a portion of an endoscope (part of the endoscope or separately formed and attached to/mounted on the endoscope). A first filament may be extendable through the first guide and along an outer surface of the endoscope; and a first endoscopic instrument may be disposable within the working channel. wherein a distal end of the first filament may be attached to a distal end of the first endoscopic instrument.

In yet another aspect, the present disclosure relates to a method comprising advancing a first instrument through a working channel of an elongate tubular member and through a lumen of a cap attached to/mounted on a distal end of the elongate tubular member such that a distal end of the first instrument may extend distally beyond a distal end of the cap.

In the described and other embodiments, a medical device attached to the distal end of the first instrument may move from a closed position to an open position. A distal end of a filament extending along an outer surface of the elongate tubular member and, optionally, cap may be attached to an arm of the medical device. The filament may extend through a guide attached to/mounted on an outer surface of the elongate tubular member or cap. The medical device may be moved from the open position to the closed position. The first instrument may be retracted such that the medical device may be disposed within the working channel of the elongate tubular member. The elongate tubular member may be advanced through a body lumen to position the distal end of the elongate tubular member or cap adjacent to a target tissue. The medical device may be advanced distally beyond a distal end of the elongate tubular member or cap. The medical device may be moved from the closed position to the open position. The medical device may be from the open position to the closed position to engage the target tissue. The medical device may be disengaged from the distal end of the first instrument. A proximal end of the filament may be proximally retracted to apply tension to the target tissue. The first instrument may be replaced with a second instrument within the working channel of the elongate tubular member. The target tissue may be manipulated with a medical device attached to a distal end of the second instrument.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to endoscopic systems and methods designed to provide traction within the gastrointestinal tract during a tissue dissection/resection procedure, it should be appreciated that such systems and methods may be used to manipulate a variety of tissues within a variety of different body lumens and/or body passages in conjunction with or independent of an endoscope.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1A:
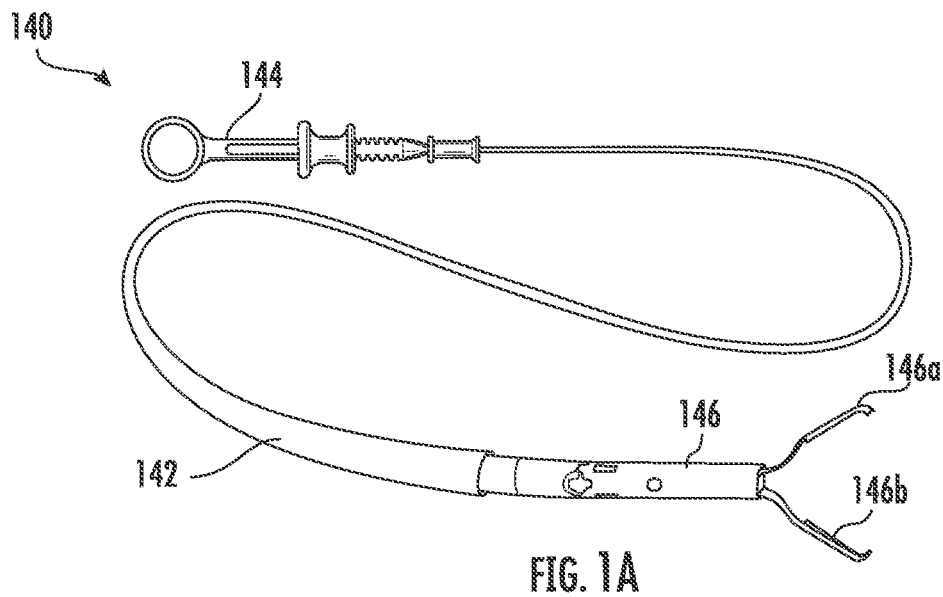
FIGS. 1A-1C provide perspective views of an instrument, according to one embodiment of the present disclosure.
Figure 1B:
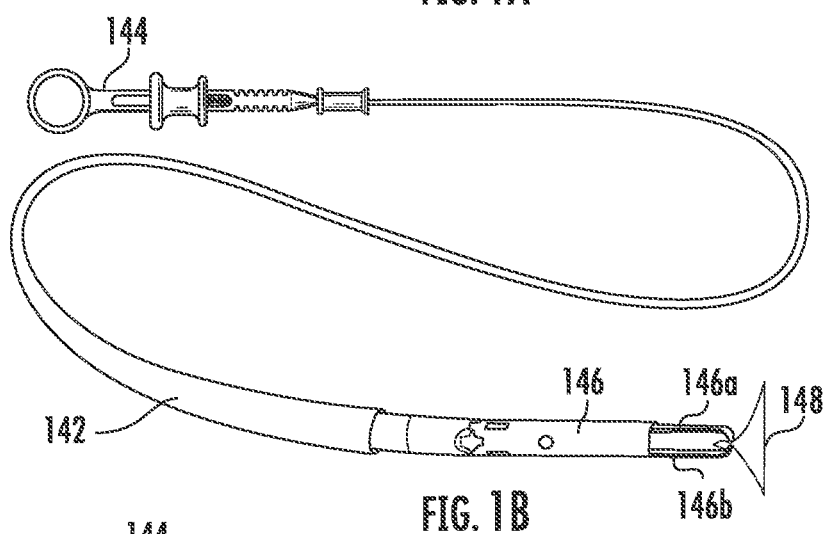
Figure 1C:
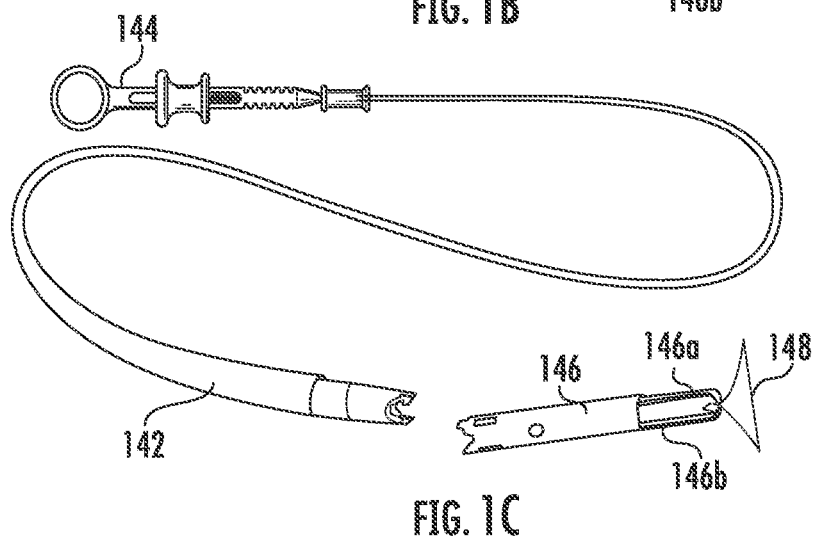

Referring to FIGS. 1A-1C, in one embodiment, a first endoscopic instrument 140 for use with an endoscopic system 100, 200, 300, 400 of the present disclosure may include a handle 144 operatively attached to a proximal end of a flexible elongate sheath 142 (e.g., catheter, etc.) and a first medical device 146 releasably attached to a distal end of the flexible elongate sheath 142. In one embodiment, the first medical device 146 may include a tissue clamp or clip comprising arms or jaws 146a, 146b configured to move upon actuation of the handle 144 between a first (e.g., open) position (FIG. 1A) and a second (e.g., closed) position (FIG. 1B). In various embodiments, in the second position the arms or jaws 146a, 146b of the first medical device 146 may engage a target tissue 148 within a body lumen, e.g., a target tissue of the gastrointestinal (GI) tract. In various additional embodiments, the handle 144 may be further actuated to disengage (e.g., release) the first medical device 146 from the distal end of the sheath 142 (FIG. 1C) such that the first medical device 146 may remain engaged with the target tissue 148 after the first endoscopic instrument 140 has been removed from within the patient.

Figure 2:
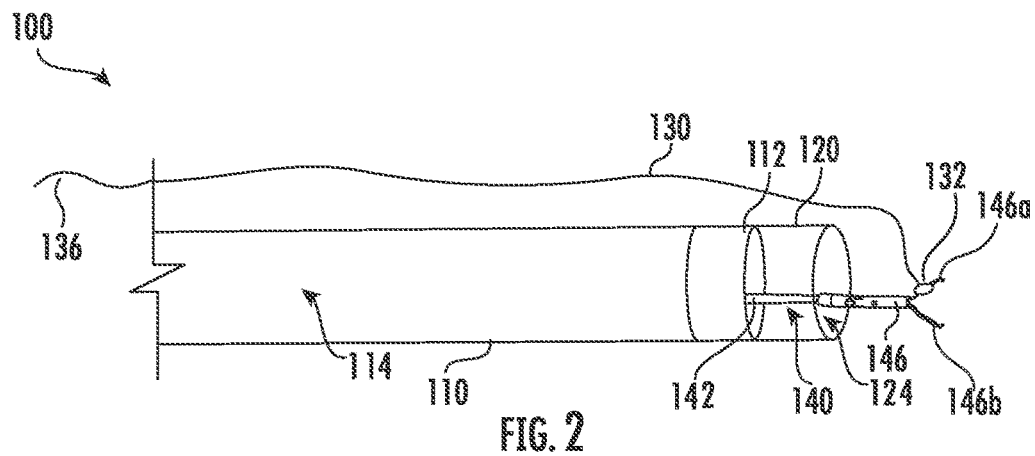
FIG. 2 provides a perspective view of a conventional tether traction system.

Referring to FIG. 2, in one embodiment, an endoscopic system 100 may include a cap 120 (e.g., endoscopic cap, etc.) attachable (e.g., by a friction or interference fit, a threaded fit, a snap-lock fit, etc.) to the distal end 112 of a flexible elongate tubular member 110 (e.g., endoscope, etc.) having a proximal end (not shown), a distal end 112, and a lumen or working channel 114 extending therebetween. A lumen 124 defined by the cap 120 may be coextensive with (e.g., aligned with) the working channel 114. A first endoscopic instrument 140 may be movably/slidably disposable within the working channel 114 and lumen 124 such that a first medical device 146 attached to a distal end of a sheath 142 of the first endoscopic instrument 140 may be extendable distally beyond the distal end of the cap 120, e.g., to engage a target tissue within a body lumen. A first filament 130 (e.g., suture, wire, string, etc.) may be extendable along an outer surface of the elongate tubular member 110 and an outer surface of the cap 120 and a distal end 132 of the first filament 130 may be attached to (e.g., tied, etc.) a portion of the first medical device 146, including, for example an arm 146a of the first medical device 146. In various embodiments, as discussed above, the first medical device 146 may be movable from the first to second positions to engage a target tissue with the first and second arms 146a, 146b and the first medical device 146 to be disengaged/released from the distal end of the sheath 142. A proximal end 136 of the first filament 130 may be extendable beyond the proximal end of the elongate tubular member 110 and external to the patient such that a medical professional may proximally retract the first filament 130 to apply tension/traction to the target tissue engaged with the first medical device 146.

Figure 3:
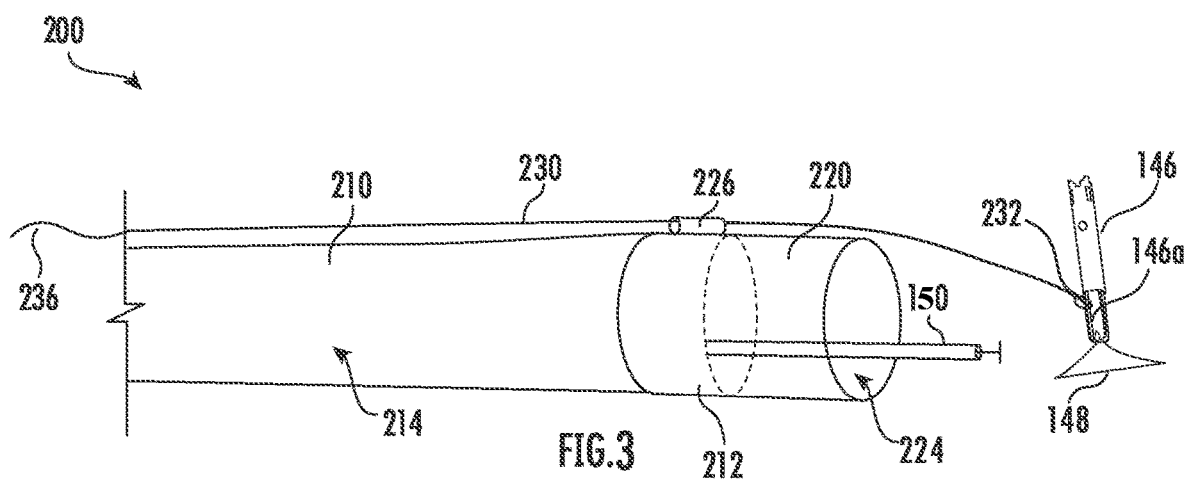
FIG. 3 provides a perspective view of a tether traction system, according to one embodiment of the present disclosure.

Referring to FIG. 3, in one embodiment, an endoscopic system 200 of the present disclosure may include a cap 220 (e.g., endoscopic cap, etc.) attachable to (e.g., by a friction or interference fit, a threaded fit, a snap-lock fit, etc.) the distal end 112 of a flexible elongate tubular member 210 (e.g., endoscope, etc.) having a proximal end (not shown), a distal end 212 and a working channel 214 extending therebetween. A lumen 224 defined by the cap 220 may be coextensive with (e.g., aligned with) the working channel 214. A first guide 226 (e.g., filament guide, suture guide, tubular support, ring, etc.) defining an open channel therethrough may be attached to/mounted on an outer surface of the cap 220. A first filament 230 (e.g., suture, wire, string, or other flexible material, etc.) may be extendable along an outer surface of the elongate tubular member 210 and an outer surface of the cap 220 and through the channel of the first guide 226.

As discussed above, a first endoscopic instrument 140 may be movably/slidably disposable within the working channel 214 and lumen 224 such that a first medical device 146 attached to a distal end of the first endoscopic instrument 140 may be extendable distally beyond the distal end of the cap 220, e.g., to engage a target tissue. A distal end 232 of the first filament 230 may be attached (e.g., tied, etc.) to an arm 146a of the first medical device 146. The first medical device 146 may then be moved from the first to second positions to engage a target tissue 148 and the first medical device 146 disengaged from the distal end of the sheath 142.

A proximal end 236 of the first filament 230 may extend beyond the proximal end of the elongate tubular member 210 and external to the patient such that a medical professional may proximally retract the first filament 230 to apply tension/traction to the target tissue 148 engaged with the first medical device 146 along a longitudinal axis of the cap 220 through the first guide 226.

Figure 4:
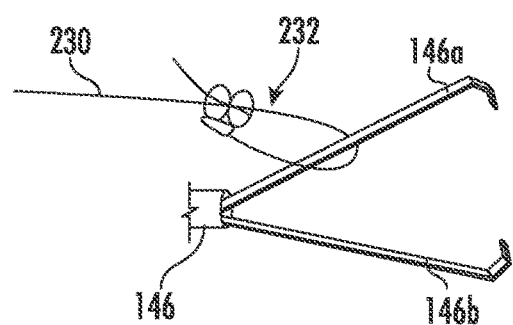
FIG. 4 provides a perspective view of a filament loop disposed around an arm of a medical device, according to one embodiment of the present disclosure.

In use, and by way of example, an endoscopic system 200 of the present disclosure may be assembled (e.g., prior to insertion into the patient) by attaching the cap 220 to the distal end 212 of the elongate tubular member 210. The first endoscopic instrument 140 may then be advanced through the working channel 214 of the elongate tubular member 210 and through the lumen 224 of the cap 220 such that the first medical device 146 attached to the distal end of the sheath 142 of the first endoscopic instrument 142 may extend distally beyond a distal end of the cap 220. The handle 144 of the first endoscopic instrument may then be actuated to move the first medical device 146 from the second position (FIG. 1B) to the first position (FIG. 1A), e.g., such that the arms 146a, 146b are open/separated in a Y-shape. The first filament 230 may then be advanced through the open channel of the first guide 226 of the cap 220 and a loop 232 formed from a distal portion of the first filament 230 may be disposed around one of the arms 146a, 146b of the first medical device 146 (FIG. 4). In one embodiment, the loop 232 may include a slip knot configured to tighten around the arm 146a when the filament 230 is proximally retracted. In some embodiments, the filament 230 may be attachable either directly or indirectly to the first medical device 146 by adhesives, soldering, welding, brazing, or mechanical attachments such as bands, clamps, or ratchet, or combinations thereof. For example, the filament 230 may be looped around the first medical device 146 and set by applying an adhesive to the filament to itself. In some embodiments, the first medical device is provided with an aperture, and an end of the filament 230 is passed through the aperture and then expanded in diameter (e.g., by knotting, heat staking, having another element coupled to, etc., the end of the filament) to maintain the end of the filament in place. The handle 144 of the first working instrument 140 may then be actuated to move the arms 146a, 146b of the first medical device 146 from the first position to the second position and the first endoscopic instrument 140 may be proximally retracted such that the first medical device 146 is disposed (e.g., protected, shielded, hidden, loaded etc.) within the lumen 224 of the cap 220 and/or the working channel 214 of the elongate tubular member 210. The endoscopic system 200, with the first medical device 146 disposed within the lumen 224 and/or working channel 214 and the first filament 230 secured to the arm 146a, may then be advanced through a body lumen of a patient and the distal end of the cap 220 positioned adjacent to a target tissue. The first endoscopic instrument 140 may then be distally advanced through the working channel 214 to position the first medical device 146 distally beyond the distal end of the cap 220. The handle 144 may then be actuated to move the arms 146a, 146b of the first medical device 146 from the second position to the first position and the open arms 146a, 146b placed in contact with a surface of the target tissue. The handle 144 may then be actuated to move the arms 146a, 146b from the first position to the second position to engage (e.g., clamp) the first medical device 146 with the target tissue. In some embodiments, the handle 144 may be actuated to disengage the first medical device 146 from the sheath 142 of the first endoscopic instrument 140. In some embodiments, the handle 144 may actuate the instrument 140 to engage with the tissue prior to and/or during a procedure.

In various embodiments, the first endoscopic instrument 140 may then be removed (e.g., withdrawn) from the working channel 214 of the elongate tubular member 210 and a second endoscopic instrument 150 may be advanced through the working channel to position a second medical device (e.g., an electrocautery knife, resection tool, etc.) attached to a distal end of the second endoscopic instrument 150 distally beyond the distal end of the cap 220 and adjacent to the target tissue 148. As discussed above, a proximal end 236 of the first filament 230 may extend beyond the proximal end of the elongate tubular member 210 and external to the patient such that a medical professional may proximally retract the first filament 230 to apply tension/traction as the second medical device manipulates (e.g., dissects) the target tissue 148.

In one embodiment, the first medical device 146 may be engaged with the portion of the target tissue being dissected such that the target tissue may be retrieved from within the patient. Alternatively, the first medical device 146 may be engaged with the target tissue adjacent to the portion being excised. In such an embodiment, the physician or other medical professional may cut the first filament (e.g., using the second medical instrument) such that the first medical device 146 may remain within the body lumen after the medical procedure is completed. The portion of the target tissue engaged by the detached first medical device 146 may eventually separate or slough off and the first medical device 146 may be expelled/removed from within the patient by the body's natural course. Alternatively, the medical professional may proximally retract the first filament with sufficient force to either break (e.g., snap) the first filament or disengage (e.g., pull free) the arms of the first medical device from the target tissue.

Figure 5:
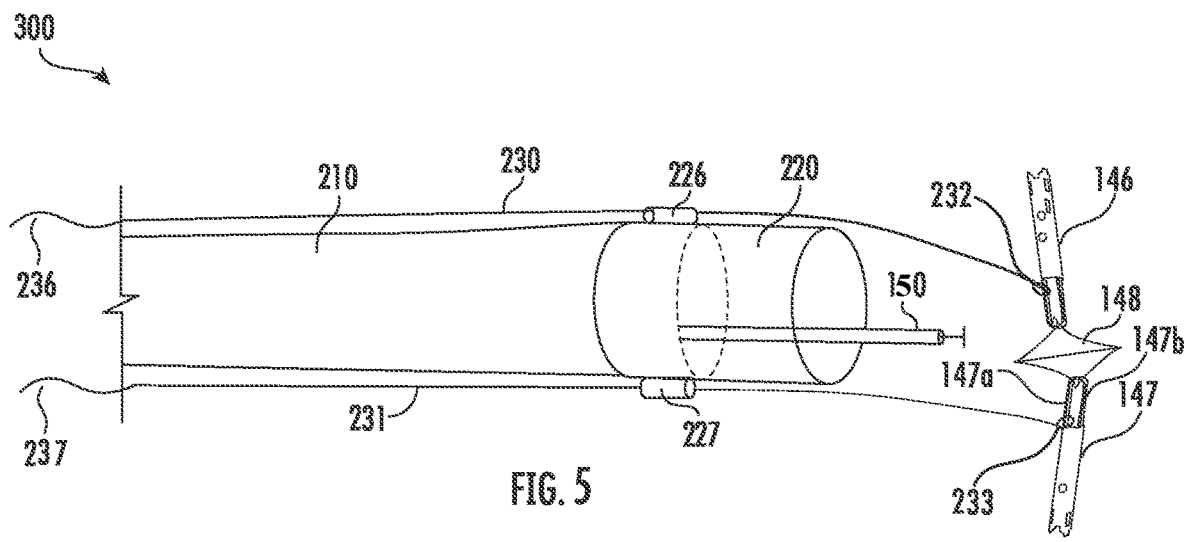
FIG. 5 provides a perspective view of a tether traction system, according to one embodiment of the present disclosure.

Referring to FIG. 5, in one embodiment, an endoscopic system 300 of the present disclosure may include the same or similar elements as endoscopic system 200, and further include a second guide 227 (e.g., suture guide, filament guide, tubular support, ring, etc.) defining an open channel therethrough attached to/mounted on the outer surface of the cap 220. Although the first and second guides 226, 227 are depicted as positioned on substantially opposite sides of the cap 220, in various embodiments the first and second guides 226, 227 may be attached to/mounted on the outer surface of the cap 220 at a variety of longitudinal and/or axial locations relative to each other. In addition, or alternatively, additional guides (e.g., third, fourth, fifth guides, etc.) may be attached to/mounted on the outer surface of the cap 220 in a variety of different patterns and/or configurations relative to each other.

In various embodiments, a second filament 231 (e.g., suture, wire, string, etc.) may be extendable along an outer surface of the elongate tubular member 210 and an outer surface of the cap 220 and through the second guide 227 such that a distal end 233 of the second filament 231 may attach to an arm 147a, 147b of a second medical device 147. In use, and by way of example, the endoscopic system 300 may be withdrawn from the patient with the first filament 230 extending through the channel of the first guide 226 and the first medical device 146 engaged with the target tissue 148. The second medical device 147 may then be attached to the distal end of the sheath 142 of the first endoscopic instrument 140, an arm 147a, 147b of the second medical device attached to the second filament 231 and the second medical device 147 loaded within the lumen 224 of the cap 220 and/or the working channel 214 of the elongate tubular member 210 by following the steps outlined above.

The endoscopic system 300, with the second medical device 147 disposable within the lumen 224 and/or working channel 214 and the second filament 231 secured to one of the arms 147a, 147b of the second medical device 147, may be reintroduced through the body lumen of the patient and the distal end of the cap 220 repositioned adjacent to the target tissue 148. The medical professional may then actuate the handle 144 as discussed above to engage (e.g., clamp) a separate portion of the target tissue 148 with the second medical device 147 and then disengage/release the second medical device 147 by following the steps outlined above with respect to the endoscopic system 200.

The first endoscopic instrument 140 may again be removed (e.g., withdrawn) from the working channel 214 of the elongate tubular member 210 and the second endoscopic instrument 150 introduced/reintroduced through the working channel to reposition the second medical device attached to a distal end of the second endoscopic instrument 150 adjacent to the target tissue. The medical professional may then proximally retract the respective proximal ends 236, 237 of the first and second filaments 230, 231 as necessary to apply the desired amount (e.g., force) and/or direction of tension/traction as the second medical device manipulates (e.g., dissects) the target tissue 148.

In one embodiment, the first and second filaments 230, 231 may include a distinguishing characteristic, such as a distinctive color code, such that the medical professional may visually identify which filament(s) to retract and/or release to properly position the target tissue for manipulation by the second medical device. For example, when viewing the target tissue through the elongate tubular member, the physician or other medical professional may identify the first filament 230 as a first color (e.g., blue) and the second filament 231 and a second color (e.g., red). The physician or other medical professional may then retract the proximal end of the first (e.g., blue) filament 230 to apply tension/retraction to the portion of the target tissue engaged with the first medical device 146 while allowing the portion of the target tissue engage with the second medical device 147 to remain slack. In addition, or alternatively, the first and second medical devices 146, 147 may include a color which matches or otherwise corresponds to the respective colors of the first and second filaments 230, 231 to which they are attached to further facilitate the medical professional's ability to apply and release tension/traction as necessary.

Although the second filament 231 is described as being attached to the second medical device 147 by first removing the endoscopic system 300 from within the patient, in various embodiments the distal end of the second filament 231 may be attached to an arm 147a, 147b of the second medical device 147 within the body lumen, e.g., by pre-loading the second filament 231 along the outer surface of the elongate tubular member 210 and cap 220 and through the channel of the second guide 227, then passing an arm of the second medical device through the loop 233 (e.g., slip-knot) of the second filament 231 within the body lumen and then proximally retracting the second filament 231 to tighten the loop 233.

Figure 6:
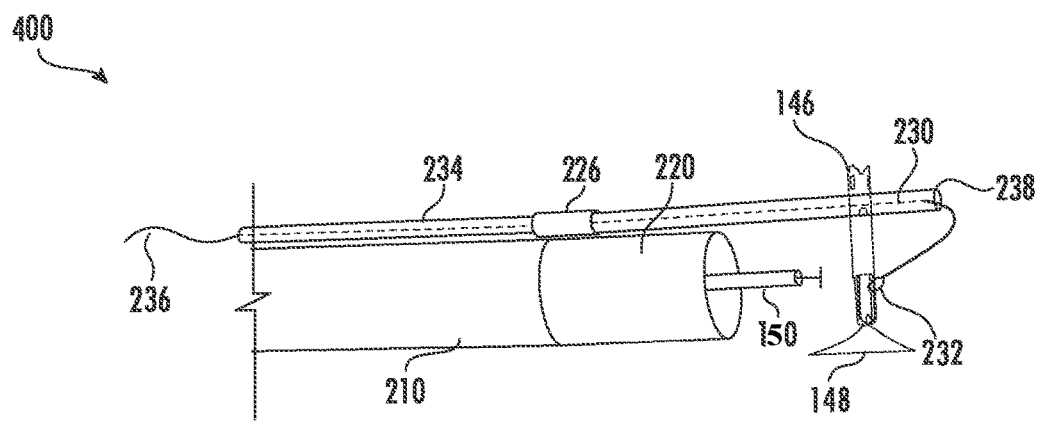
FIG. 6 provides a perspective view of a tether traction system, according to one embodiment of the present disclosure.

Referring to FIG. 6, in one embodiment, an endoscopic system 400 of the present disclosure may include the same or similar elements as endoscopic systems 200, 300 and further include a flexible elongate shaft 234 extendable along an outer surface of the elongate tubular member 210 and cap 220 and through the channel of the first guide 226. In various embodiments, the flexible elongate shaft 234 may be slidably and/or rotatably disposable within the first guide 226 such that a distal end 238 of the flexible elongate shaft 234 may be extended distally beyond a distal end of the cap 220. A first filament 230 may be extendable through a full length of the flexible elongate shaft 234 such that a distal end 232 of the first filament 230 may be attached to an arm of a first medical device 146 and a proximal end 236 of the first filament 230 may extend outside the patient, as discussed above. In various embodiments, the flexible elongate shaft 234 may include sufficient rigidity (e.g., columnar strength) such that a medical professional may distally advance the flexible elongate shaft 234 through the channel of the first guide 226 to apply tension/traction to the first medical device 146 engaged with a target tissue 148 in a direction opposite to (e.g., distally away from) the distal end of the cap 220.

Although the endoscopic system 400 is described as including a single flexible elongate shaft 234 extendable along an outer surface of an endoscope that includes a cap 220 with a first guide 226 attached/mounted thereto, in various embodiments an endoscopic system of the present disclosure may include a cap with more than one guide attached/mounted thereto (e.g., first and second guides 226, 227 of system 300), each of which may slidably and/or rotatably receive separate flexible elongate shafts therethrough. In various additional embodiments, an endoscopic system of the present disclosure that may include multiple guides (e.g., first and second guides 226, 227 of system 300) attached to/mounted on the outer surface of the cap 220 may include a flexible elongate shaft extending through one of the guides and a filament without a flexible elongate shaft extending through the other guide, e.g., to allow the physician to apply tension/traction in the proximal and distal directions relative to the distal end of the cap. In various additional embodiments, a flexible elongate shaft 234 of the present disclosure may be advanced over a first or second filament 230, 231 of the present disclosure and through the respective channel of the first or second guides 226, 227 while a medical device attached to the distal end of that filament is engaged with a target tissue, e.g., to allow the physician to switch the direction of tension/traction applied to the target tissue.

Figure 7:
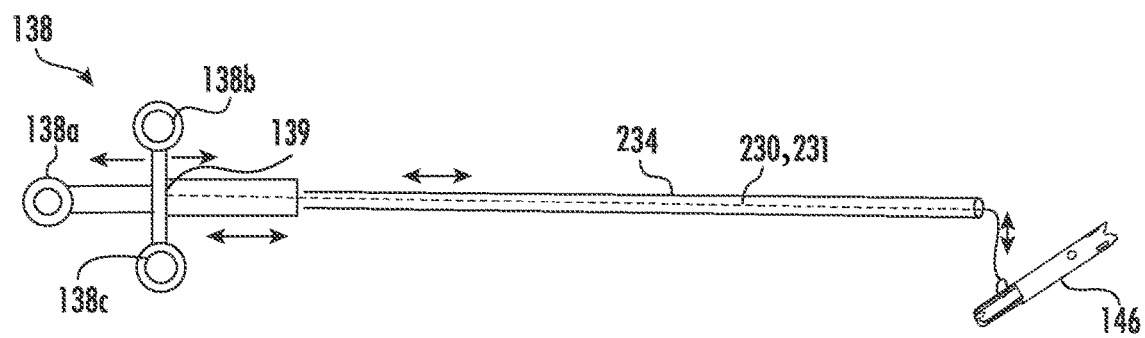
FIG. 7 provides a perspective view of a handle assembly of a flexible elongate shaft, according to one embodiment of the present disclosure.

Referring to FIG. 7, in one embodiment, a proximal end of a flexible elongate shaft 234 of the present disclosure may be attached to a handle assembly 138. In various embodiments, the handle assembly 138 may include a first gripping element 138a (e.g., thumb ring), a second gripping element 138b (e.g., first finger ring) and a third gripping element 138c (e.g., a second finger ring). The first gripping element 138a may be attached to the proximal end of the flexible elongate shaft 234 and the second and third gripping elements 138b, 138c may be pivotably and/or slidably attached to the handle assembly 138 by a connecting arm 139. A proximal end of a filament (e.g., first or second filaments 230, 231) of the present disclosure may be attached (e.g., tied, glued, etc.), either directly or indirectly, to the connecting arm 139 between the second and third gripping elements 138b, 138c. In one embodiment, a medical professional may hold the handle assembly 138 in their hand and proximally retract and/or distally advance the flexible elongate shaft 234 through the channel of a guide (e.g., first or second guides 226, 227) of the present disclosure using the first gripping element 138a, e.g., to apply or release tension/traction of the filament in a distal direction relative to the distal end of the cap 220. In addition, or alternatively, the medical professional may proximally retract and/or distally extend the filament through the guide by longitudinally pivoting and/or sliding the second and third gripping elements 138b, 138c relative to the handle assembly 138 (e.g., in a back-and-forth direction). In various embodiments, the first gripping element 138a may provide coarse/gross control of the flexible elongate shaft 234, e.g., to position or reposition the distal end 238 of the flexible elongate shaft relative to the target tissue, and the second and third gripping elements 138b, 138c may provide fine-tune/incremental control of the filament to precisely manipulate the target tissue.

Figure 8:
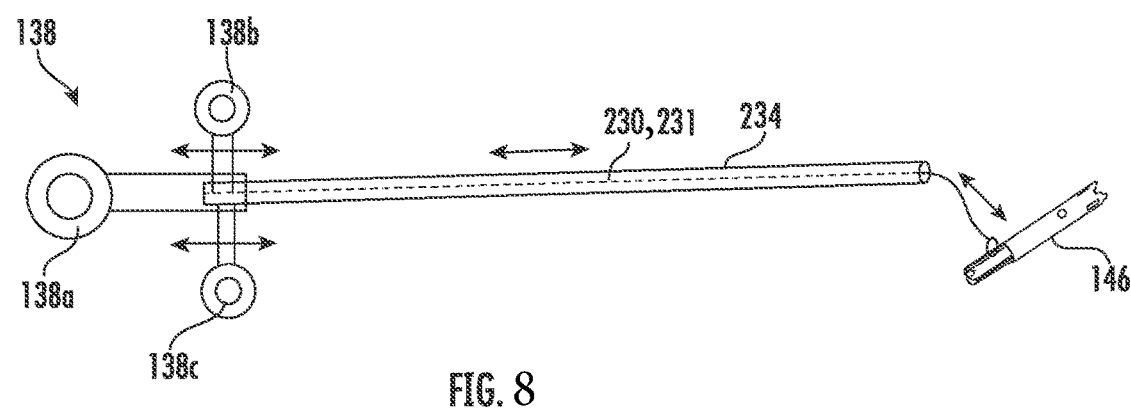
FIG. 8 provides a perspective view of a handle assembly of a flexible elongate shaft, according to one embodiment of the present disclosure.

Referring to FIG. 8, in one embodiment, a handle assembly 138 of the present disclosure may include the same or similar elements as the handle assembly of FIG. 8, but with second and third gripping elements 138b, 138c that are independently actuatable (e.g., not attached by a connecting arm, etc.). In one embodiment, the second gripping element 138b may be pivotably and/or slidably attached to a proximal end of a filament (e.g., first or second filaments 230, 231) of the present disclosure and the third gripping element 138c may be pivotably and/or slidably attached to a proximal end of the flexible elongate shaft 234. In various embodiments, the first gripping element 138a may provide coarse/gross control of the flexible elongate shaft 234 (as discussed above), and the second and third gripping elements 138b, 138c may provide fine-tune/incremental control of the filament and flexible elongate shaft independent of each other. For example, the second gripping element 138b may be actuated to move the filament relative to (e.g., in a back-and-forth direction) the flexible elongate shaft and/or the third gripping element 138c may be actuated to move the flexible elongate shaft relative to (e.g., in a back-and-forth direction along a longitudinal axis) the filament.

Although the first and second guides 226, 227 of the present disclosure are depicted as positioned adjacent to a proximal end of the cap 220, in various embodiments the first and second guides 226, 227 may be attached to/mounted on the outer surface of the cap 220 at a variety of locations (e.g., a mid-point of the cap, a proximal end of the cap, etc.). In addition, or alternatively, the first and second guides 226, 227 may extend a full length of the cap 220 and/or extend distally beyond the distal end of the cap 220.

In addition, although first and second guides of the present disclosure are described as associated with (e.g., attached to, mounted on) an outer surface of a cap 220, and the above-described embodiments are described with reference to a cap element, it will be appreciated that the principles of the above disclosure are applicable to each embodiment even if a cap element is not provided. As such, references to a cap on a structure should be understood to include references to an element which is a part of (unitary or separate) the distal end of the structure. For instance, in various embodiments the guides may be provided along or attached to/mounted on an outer surface of the flexible elongate tubular member either with or without a cap 220 attached thereto. As above, the guide(s) may be distributed along the outer surface of the flexible elongate tubular member in a variety of different patterns, orientations and/or numbers, such as those described with reference to a cap. For example, a series of guides may be disposed along an outer surface of the flexible elongate tubular member in evenly or unevenly spaced intervals along a longitudinal or non-longitudinal axis thereof. In some embodiments, the guides may extend along an entire outer surface of the flexible elongate tubular member and/or the cap, e.g., to provide a contiguous enclosed channel through which the filament(s) may extend. In some embodiments, the guides may include one or more straps or bands disposed around various circumferential portions of the outer surface of the flexible elongate tubular member and/or cap. Additionally or alternatively, a flexible elongate shaft is extendable along an outer surface of the elongate tubular member regardless of whether a cap is present. In some embodiments, a flexible elongate shaft is extendable through a guide extending along or mounted on the outer surface of an elongate tubular member. A filament may extend through any of the above embodiments, such as through the guide and/or flexible elongate shaft of any of the above embodiments.

In various embodiments, the second medical device of the present disclosure is not limited to a tissue cutting element (e.g., electrocautery knife, etc.), but may include a variety of medical instruments configured to manipulate a target tissue (e.g., ablative elements, needles or syringes configured to inject agents into the target tissue, etc.).

In various additional embodiments, the first and second medical devices 146, 147 of the present disclosure herein may include a variety of hemostasis and non-hemostasis tissue clips configured to secure/engage the first and second filaments 230, 231 to the target tissue. For example, a tissue clip contemplated for use with the disclosed endoscopic systems 200, 300, 400 may include a naturally open/biased configuration configured to move to a closed/clamped configuration upon actuation by a handle assembly. In addition, or alternatively, a tissue clip contemplated for use with the disclosed tissue retraction/traction device may include a naturally closed/biased configuration configured to move an open configuration upon actuation by a handle assembly. In addition, or alternatively, fasteners other than the described tissue clips may be used to secure/engage the first and second attachment members of the disclosed tissue retraction/traction device to the wall of a body lumen. Examples of fasteners may include, but are not limited to, those described in U.S. Pat. No. 10,952,717, issued May 13, 2020, and titled "Tissue Traction Bands and Methods of Use Thereof"; U.S. Patent Application Publication No. 2020/0129181, filed Oct. 30, 2019, and titled "Clip Devices, Systems, and Methods for Engaging Tissue"; U.S. Pat. No. 11,147,564, issued May 13, 2020, and titled "Tissue Clip Devices, Systems, and Traction Methods"; U.S. Patent Application Publication No. 2018/0263614, filed Mar. 19, 2018, and titled "Tissue Retraction Device and Delivery System"; and U.S. Pat. No. 8,062,311, issued Nov. 22, 2011, and titled "Endoscopic Hemostatic Clipping Apparatus", all of which are herein incorporated by reference in their entireties for all purposes. Other features and aspects of these patents and patent applications, as well as U.S. Patent Application Publication No. 2020/0360006, filed on May 13, 2020, and titled "Tissue Traction Bands And Methods For Tissue Traction", which application is herein incorporated by reference in its entirety for all purposes, may complement devices and methods of the present disclosure and may be used therewith.

In addition, it should be appreciated that the first and second medical devices 146, 147 of the present disclosure are not necessarily drawn to scale, but may be represented in a somewhat enlarged configuration to provide the requisite level of detail to understand and practice the embodiments of the present disclosure.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for use with a flexible elongate tubular member extendible within and through a patient and having a working channel therethrough, the system comprising:
   a cap attachable to a distal end of the flexible elongate tubular member and having a working channel extending therethrough, the cap including a lumen coextensive with the working channel of the flexible elongate tubular member;
   a first guide attached to an outer surface of the cap; and
   a first filament extendable through the first guide and along an outer surface of the flexible elongate tubular member and the cap such that the filament and the outer surface of the flexible elongate tubular member may contact each other.

2. The system of claim 1, wherein the first filament extends through the first guide without an additional element therearound.

3. The system of claim 1, wherein the first filament is extendable proximally outside the patient to be retractable by a physician.

4. The system of claim 1, further comprising:
   a second guide attached to an outer surface of the cap;
   a flexible elongate shaft extendable along the outer surface of the flexible elongate tubular member and the cap and through the second guide; and
   a second filament extendable through the flexible elongate shaft and along an outer surface of the flexible elongate tubular member while within the flexible elongate shaft.

5. The system of claim 1, wherein the flexible elongate tubular member is an endoscope.

6. The system of claim 5, further comprising a first endoscopic instrument extending through the working channel of the flexible elongate tubular member.

7. The system of claim 6, wherein the first filament is extendable from a first end attached to a distal end of the first endoscopic instrument to a second end extended outside the patient and retractable by a physician.

8. A system for performing an endoscopic procedure within a patient, the system comprising:
   a first guide extendable along at least a portion of an outer surface of an endoscope, the endoscope having a working channel extending therethrough with an open distal end through which an endoscopic instrument is extendable; and
   a first filament having a distal end and a proximal end and extendable from the distal end at the open distal end of the endoscope, directly through the first guide, and proximally and directly along an outer surface of the endoscope to outside the patient to the proximal end to be controlled by a physician.

9. The system of claim 8, further comprising a first endoscopic instrument extending through the working channel of the endoscope.

10. The system of claim 9, wherein the distal end of the first filament is attached to a distal end of the first endoscopic instrument.

11. The system of claim 8, further comprising a second guide extending along a portion of the outer surface of the endoscope and a second filament extending through the second guide and along an outer surface of the endoscope.

12. The system of claim 11, further comprising a flexible elongate shaft extendable along the outer surface of the endoscope and through the second guide, wherein the second filament extends through the flexible elongate shaft.

13. The system of claim 11, further comprising:
   a first endoscopic instrument extendable through the working channel of the flexible tubular elongate member and couplable with the distal end of the first filament; and
   a second endoscopic instrument extendable through the working channel of the flexible tubular elongate member and couplable with the distal end of the second filament.

14. A method, comprising:
   extending a first filament along an outer surface of a flexible elongate tubular member from a distal end of the flexible elongate tubular member, through a first guide mounted on an outer surface of the flexible elongate tubular member, and along an outer surface of the flexible elongate tubular member without a further element between the first filament and the first guide or the outer surface of the flexible elongate tubular member;
   coupling a distal end of the first filament to target tissue; and
   retracting the first filament via a proximal end of the first filament to apply traction to the target tissue.

15. The method of claim 14, wherein extending the first filament through the first guide comprises extending the first filament directly through the first guide without an additional element therearound.

16. The method of claim 14, wherein the target tissue is within a patient, the method further comprising extending the proximal end of the first filament outside the patient to be retracted manually.

17. The method of claim 14, further comprising advancing the flexible elongate tubular member internally through a body lumen within a patient to position the distal end of the flexible elongate tubular member adjacent to a target tissue and to couple the distal end of the first filament to the target tissue.

18. The method of claim 17, further comprising:

advancing a first medical instrument with a first medical device through a working channel extending through the flexible elongate tubular member to advance the first medical device out a distal open end of the working channel;

coupling the distal end of the first filament to the first medical device; and coupling the first medical device to the target tissue to couple the first filament to the target tissue.

19. The method of claim 17, further comprising:

disengaging the medical device from the first medical instrument;

extending a second medical instrument with a second medical device through the working channel of the flexible elongate tubular member;

coupling a distal end of a second filament to the second medical instrument;

extending the second filament along an outer surface of the flexible elongate tubular member from the distal end of the flexible elongate tubular member, through a second guide mounted on an outer surface of the flexible elongate tubular member, and along an outer surface of the flexible elongate tubular member to extend the proximal end of the second filament outside the patient's body.

20. The method of claim 19, further comprising:

coupling the second medical instrument to tissue within the patient; and proximally retracting the proximal end of the second filament to apply tension to the second medical instrument and the tissue coupled thereto.

* * * * *